(12) United States Patent
Garth et al.

(10) Patent No.: US 8,216,167 B2
(45) Date of Patent: Jul. 10, 2012

(54) CERVICAL-THORACIC ORTHOTIC WITH CERVICAL COLLAR

(76) Inventors: Geoffrey C. Garth, Long Beach, CA (US); Wayne Calco, Laguna Hills, CA (US); Jozsef Horvath, Fullerton, CA (US); Erik Zimmer, Oceanside, CA (US)

(*) Notice: Subject to any disclaimer, the term of this patent is extended or adjusted under 35 U.S.C. 154(b) by 442 days.

(21) Appl. No.: 12/469,966

(22) Filed: May 21, 2009

(65) Prior Publication Data
US 2010/0298749 A1 Nov. 25, 2010

(51) Int. Cl.
*A61F 5/00* (2006.01)
(52) U.S. Cl. .......................... 602/18; 602/19
(58) Field of Classification Search .............. 602/17–19; 128/DIG. 23
See application file for complete search history.

(56) References Cited

U.S. PATENT DOCUMENTS

| | | | |
|---|---|---|---|
| 2,223,276 A * | 11/1940 | Ward | 602/18 |
| 2,904,040 A * | 9/1959 | Hale | 602/18 |
| 5,964,722 A | 10/1999 | Goralnik et al. | |
| 6,921,376 B2 | 7/2005 | Tweardy et al. | |
| 7,549,970 B2 * | 6/2009 | Tweardy | 602/18 |
| 2003/0220594 A1 * | 11/2003 | Halvorson et al. | 602/19 |
| 2005/0159692 A1 | 7/2005 | Tweardy | |

FOREIGN PATENT DOCUMENTS
WO  2005122725  12/2005
* cited by examiner

*Primary Examiner* — Michael A. Brown
(74) *Attorney, Agent, or Firm* — Fish & Associates, PC

(57) ABSTRACT

An orthosis comprises a cervical portion that holds a head in place relative to a thoracic portion worn by a wearer. The orthosis has an intermediate portion disposed intermediate the cervical and thoracic portions. The orthosis also has a first adjustment region that provides at least 15° of relative movement between the cervical and intermediate portions, and a second adjustment region that provides at least 15° of relative movement between the thoracic and intermediate portions. First and second adjustment regions allow the orthosis to comfortably accommodate differently proportioned wearers, and each comprises one or more locking devices to prevent undesired movement of the cervical and thoracic portions relative to the intermediate portion.

20 Claims, 4 Drawing Sheets

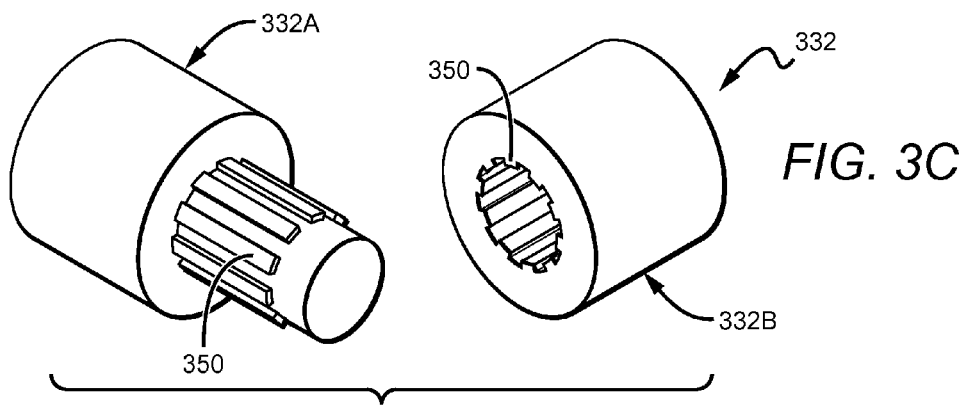

*FIG. 3C*

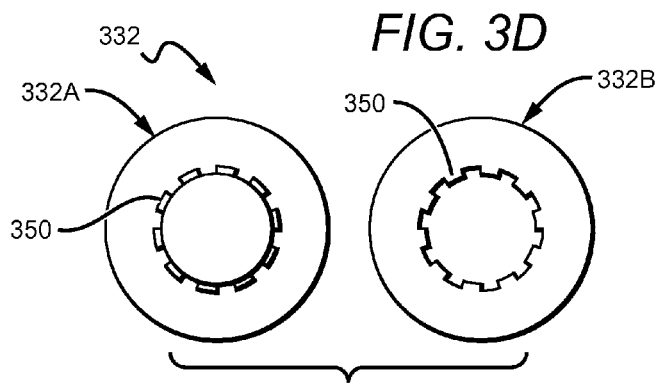

```
┌─────────────────────────────────────┐
│  Coupling the cervical and thoracic │
│  orthotics with first and second    │
│  pivots to define a cervico-thoracic│
│  orthotic                           │
└──────────────┬──────────────────────┘
               │   ┌─────────────────────────────────┐
               │   │ Disposing first and second      │
               ├---│ intermediate pieces between the │
               │   │ cervical and thoracic orthotics.│
               │   └─────────────────────────────────┘
               │   ┌─────────────────────────────────┐
               │   │ Providing a telescoping region  │
               ├---│ between the cervical and        │
               │   │ thoracic orthotics.             │
               │   └─────────────────────────────────┘
┌──────────────┴──────────────────────┐
│ Operating the cervico-thoracic       │
│ orthotic such that each of the pivots│
│ is continuously operable while the   │
│ cervico-thoracic orthotic is being   │
│ adjusted.                            │
└──────────────────────────────────────┘
```

CERVICAL-THORACIC ORTHOTIC WITH CERVICAL COLLAR

FIELD OF THE INVENTION

The field of the invention is cervical orthotics.

BACKGROUND

Orthotics are typically custom-fitted devices designed to provide support for muscles or other tissues that have been damaged or weakened in some manner, as for example by injury or disease. Cervical thoracic orthotics (CTOs) are particularly designed to provide support to the head, and cervical and thoracic spine. Because wearers can have profoundly different proportions, orthotics are generally made in multiples sizes. This can be time consuming and expensive to medical practitioners who have to stock and keep track of the different sizes.

Adjustable orthotics have been designed to address the problems associated with multiple-sized orthotics. For example, U.S. Pat. No. 5,964,722 to Goralnik, et al. teaches a cervical thoracic brace having a collar with parts coupled by detachable straps. Although the detachable straps allow the collar portion to be adjusted to the wearer, the brace fails to provide any relative movement between the cervical and thoracic portions. Goralnik and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

In an attempt to provide a CTO that allows some relative movement of the cervical and thoracic portions, U.S. Pat. No. 6,921,376 to Tweardy et al. describes a cervical brace that wraps around the collar, and can be connected to a thoracic portion by means of a rear strut. The cervical brace is supported by a chin strut and an anterior plate assembly that can be slidably connected to the cervical brace. The Tweardy device allows for superior/inferior (up/down) movement of the cervical portion relative to the thoracic portion, but fails to allow for angular adjustment of the cervical and thoracic portions. That failure can prevent the device from properly fitting certain patients, including especially those having an extreme kyphosis of the upper thoracic spine, and/or obese patients.

U.S. Pat. No. 2,223,276 to Ward describes a CTO having cervical and thoracic pieces that are sagittally adjustable relative to one another by pivotally intermediate pieces ("irons") relative to one another. One problem, however, is that the pivot points of Ward's intermediate pieces merely provide tightening, not splines or other locking mechanisms. Another problem is that Ward's tightening mechanism may require application of considerable torque to provide effective tightening, and even with such effort, a sudden application of force, such as by a fall or other wearer's movement, could readily alter the desired configuration.

Thus, there is still a need for CTOs that allows for sagittal adjustment between the cervical and thoracic portions, but that also has splines or other locking devices sufficient to prevent undesired or unintentional movements of the cervical and thoracic portions.

SUMMARY OF THE INVENTION

The inventive subject matter provides apparatus and methods in which a CTO has one or more intermediate connector pieces disposed between the cervical and thoracic portions, and having pivot points that are lockable by spline or other mechanism(s).

As used herein, the term "disposed between" means functionally disposed between. Thus, a connector piece could be disposed between cervical and thoracic portion even though it has no direct connection to either of the cervical or thoracic portions.

In a preferred embodiment, the intermediate portion has a superior and an inferior end, and sufficient rigidity to maintain a fixed angular relationship between the ends within a 10° tolerance. Such intermediate portions advantageously allow for coupling of the cervical and thoracic portions in many different configurations, while the rigidity severely constrains relative sagittal movement of the head and neck relative to the upper torso.

Intermediate portions can comprise any commercially practical length, which in practice is likely at least 10 cm from end to end. Smaller dimensions are also contemplated, but would tend to limit the range of adjustability. Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

Preferred CTOs also have a cervical portion that both limits movement of the neck and provides support for the head by transferring some or all of the load to the shoulders. Most preferably, the cervical portion would limit the head and neck from moving in all directions, sagittal and lateral flexion and extension, and rotation. Exemplary cervical portions are cervical collars found in U.S. Pat. No. 7,141,031 to Garth et al. and U.S. Pat. Appl. No. 2007/0027418 to Calco et al. (pub. February 2007).

Preferred CTOs also have a thoracic portion coupled to the cervical portion. If the cervical portion is not a collar, the thoracic portion provides additional support and stability to the cervical portion. However, if the cervical portion is a collar, the thoracic portion effectively holds a wearer's head in place relative to the wearer's chest. Exemplary thoracic portions are discussed in U.S. Pat. No. 6,315,746 to Garth et al. and U.S. Pat. No. 3,724,452 to Nitschke. The thoracic portion is preferably coupled to the wearer via a strap that wraps around the front of the wearer. Advantageously, the thoracic portion could be coupled to the cervical portion using a quick release mechanism.

At least one of the intermediate and thoracic portions can comprise a telescoping region to allow the CTO to be adjusted to accommodate various torso lengths of wearers.

Preferred CTOs also have a first adjustment region that provides at least 15° of relative movement between the cervical and intermediate portions, and a second adjustment region that provides at least 15° of relative movement between the thoracic and intermediate portions. These adjustment regions allow the cervical and thoracic portions to be coupled while being worn in such a way as to fit by differently sized and shaped wearers without the need for additional equipment such as bending irons. More preferably, at least one of the regions, and preferably both, provide at least 25° of relative movement, and most preferably, 30° of relative movement between their respective portions.

Contemplated adjustment regions comprise one or more commercially suitable locking device(s) to prevent unintentional or undesired movement of the adjustment regions. This advantageously allows the cervical, intermediate, and thoracic positions to be continuously adjusted and then locked in place once fitted to a wearer's body shape. Still further, the locking device(s) allow the portions to remain locked in place even after a sudden force such as that resulting from a wearer's fall. Each of the locking devices preferably comprise first and second splines, which can be internal, external, lateral, and/or have any commercially suitable configurations. Contemplated splines could comprise any commercially suitable coarseness, and preferred splines have a coarseness of between 10-30 positions or teeth.

Preferred locking devices can be "opened" (e.g., released) by a button or other release. Thus, for example, the adjustment region could be biased open by the inclusion of a spring or other elastic device configured to be compressed as the adjustment region is "closed" (e.g., locked in place). Once the releasing device is actuated, the spring pushes the locking device(s) to an "open" position. However, it is also contemplated that the adjustment region could be biased closed. Thus, for example, a spring could be positioned such that the spring is compressed as the locking device is moved to an "opened" or unlocked position. Once the locking device is released, the spring operates to push the locking device to the "closed" position. Alternatively or additionally, the intermediate portion could include one or more locking devices.

The adjustment regions can advantageously comprise a pivot, although any equivalent structure could be used for one or both of the regions including for example, a flexible or bendable portion or any combination thereof. As used herein, the term "pivot" includes mechanisms that provide pivoting motion, even though there is no actual axis about which the pivoting motion takes place. Thus, for example, cervical portion can be said to be pivotally mounted to intermediate piece at a pivot even in situations where these parts are molded together in a manner that provides sufficient "play" to effectively provide a pivoting-type motion.

Additionally, contemplated CTOs could advantageously include an adapter portion disposed between the cervical and intermediate portions that allows for quick coupling and decoupling of the cervical and intermediate portions. In one aspect, an end of the adaptor could form one arm of the pivot, and the intermediate portion could form the other arm of the pivot. The adapter portion can be coupled to the cervical portion using any commercially suitable fastener(s) including for example, mechanical fasteners (e.g., hook and loop fasteners, buckles, clips, clasps, screws, etc.), non-mechanical fasteners (e.g., adhesives, magnets, etc.), and/or any combinations thereof. Preferred adapter portions utilize at least one clip (e.g., snap) to removably attach the adaptor portion to the cervical portion.

In another aspect, a method of coupling a cervical orthotic with a thoracic orthotic on a wearer comprises coupling the cervical and thoracic orthotics with first and second pivots to produce a CTO. In a contemplated embodiment, first and second intermediate pieces could be disposed between the cervical and thoracic orthotics to facilitate coupling of the orthotics. Once produced, the CTO can be operated to allow each pivot to be continuously operable while the CTO is adjusted. Once adjusted, the locking device(s) can be engaged to lock the orthotics in place. Preferably, the CTO also comprises a telescoping region which could be ideally situated between the cervical and chest panel portions.

Various objects, features, aspects and advantages of the inventive subject matter will become more apparent from the following detailed description of preferred embodiments, along with the accompanying drawings in which like numerals represent like components.

BRIEF DESCRIPTION OF THE DRAWINGS

FIGS. 3C and 3D are enlarged side and frontal views, respectively, of a locking device.

FIG. 4 is a flowchart illustrating a method of coupling a cervical and thoracic orthotic on a wearer.

DETAILED DESCRIPTION

Figure 1:
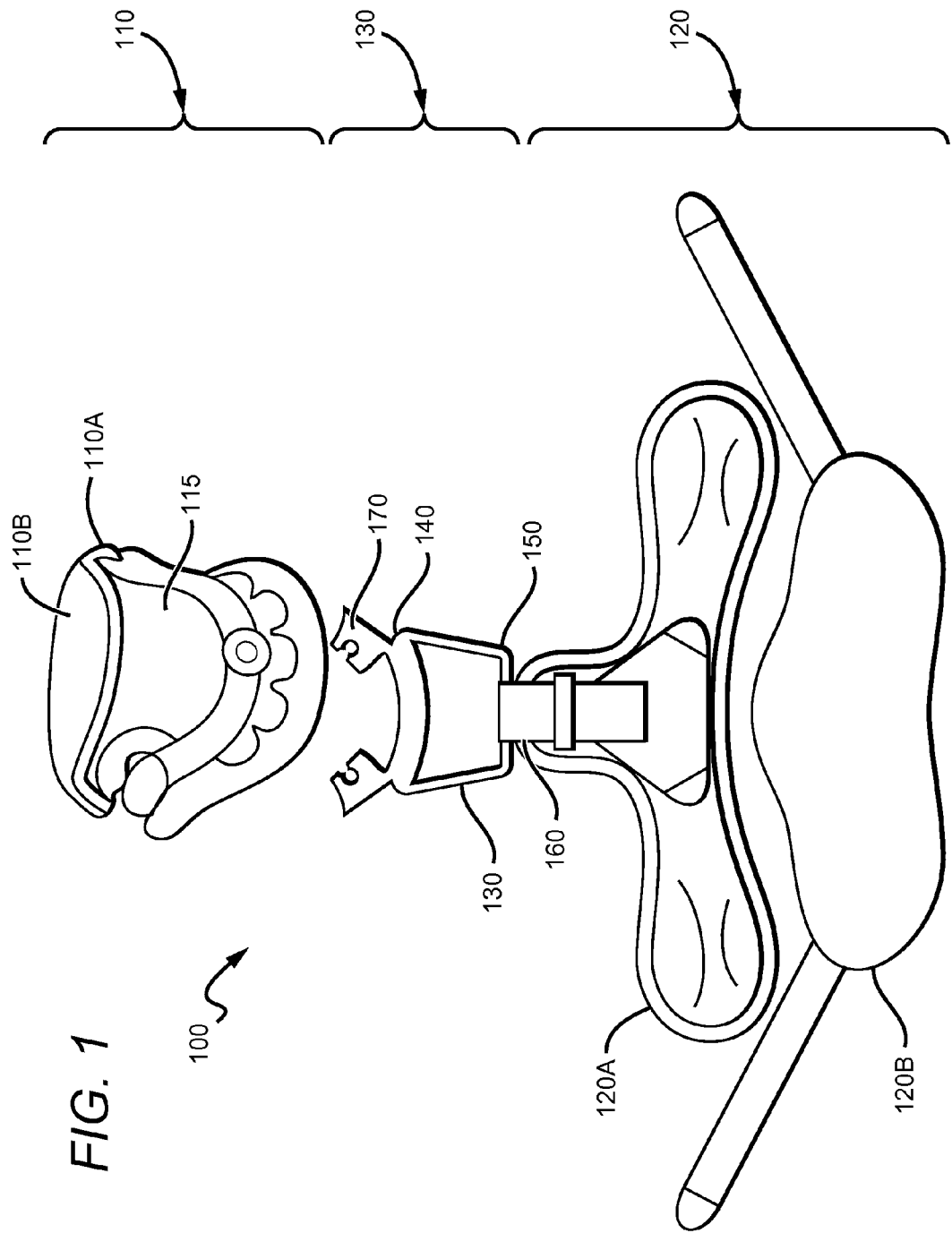
FIG. 1 is an illustration of an embodiment of a CTO.
Figure 2:
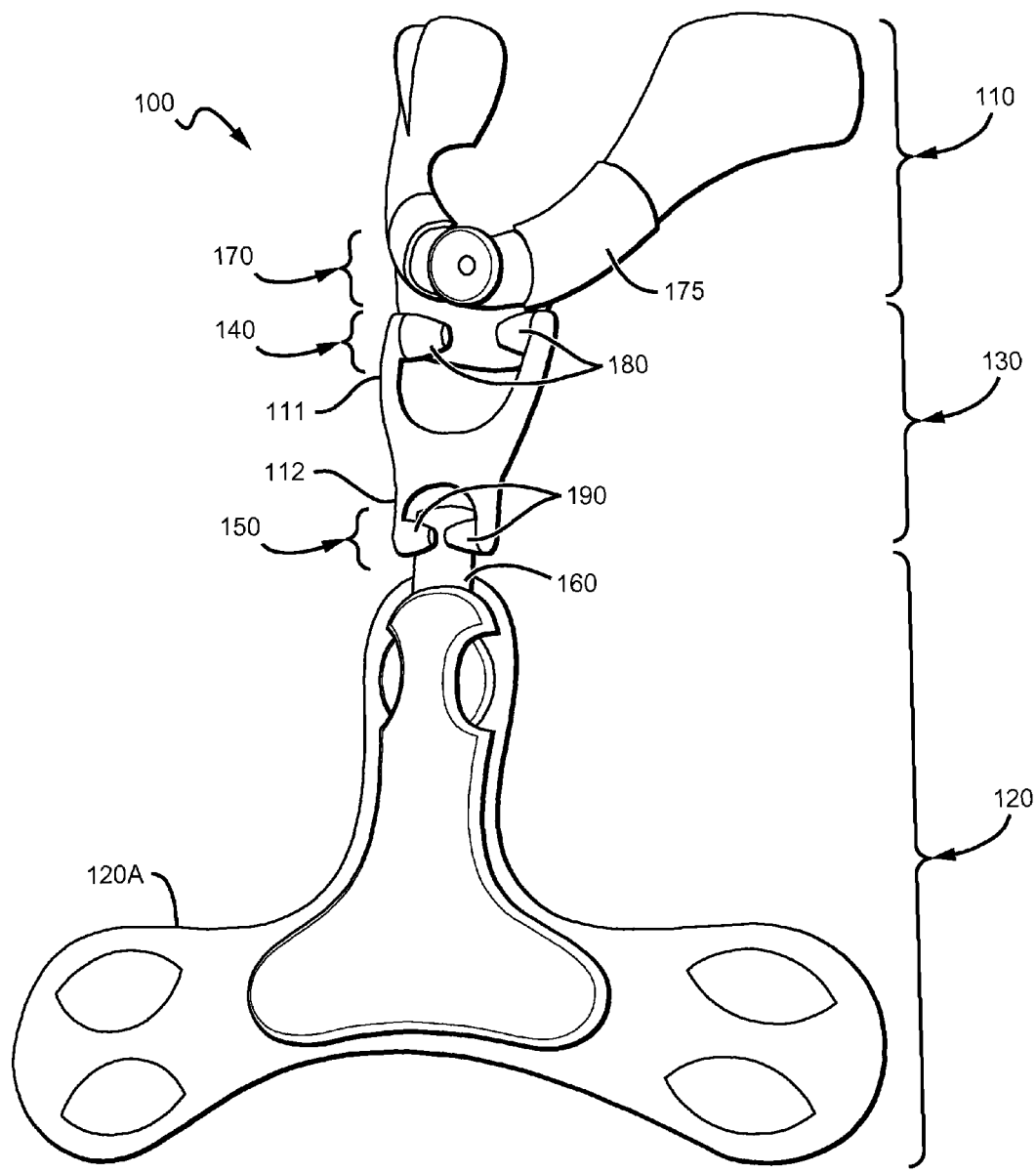
FIG. 2 is an enlarged illustration of the CTO of FIG. 1.

In FIGS. 1-2, a CTO 100 generally comprises a cervical portion 110, a thoracic portion 120, an intermediate portion 130, and first and second adjustment regions 140 and 150, respectively.

As shown in FIG. 1, cervical portion 110 comprises chin support 110A and an occipital support 110B that limit motion of the head and neck. Contemplated cervical portions can comprise any commercially suitable orthotics that operate to limit lateral movement of a wearer's head and neck. Optionally, cervical portion 110 could also comprise an upper head brace (not shown) to support a forehead strap. Additionally, cervical portion 110 can include opening 115 to allow access to the trachea of the wearer.

Thoracic portion 120 comprises abdominal 120A and lumbar 120B supports. In this embodiment, the thoracic portion advantageously provides support for both the lumbar region of the wearer, and the cervical portion 110.

Thoracic portion 120 further comprises telescoping region 160 to allow vertical adjustment of CTO 100 to accommodate wearers of different torso lengths. Telescoping region 160 preferably includes adjuster 165 to increase or decrease the overall CTO length as desired. Contemplated telescoping regions can be adjusted to any commercially practical length, and preferably have an adjustable length of at least 15 cm, and more preferably at least 30 cm.

In embodiments shown in FIGS. 1-2, the distance between the cervical and thoracic portions can be adjusted by rotating adjuster 165, which causes rotation of a pinion gear (not shown) and vertically adjusts the telescoping region 160. Preferably, such rotation is bi-directional with one direction (e.g., clockwise) causing the telescoping region 160 to move upward and the other direction (e.g., counter-clockwise) causing the telescoping region 160 to move downward. It is also contemplated that translation of the telescoping region could be limited by limiting rotation of the pinion gear, such as through the use of a pin within a slot (not shown). While adjuster 165 is shown as a rotatable knob, alternative adjusters include, for example, screws, clips, etc. In alternative embodiments, telescoping region could operate without an adjuster, such as by releasing the telescoping region and pulling the region away from the thoracic portion.

Intermediate portion 130 is disposed between the cervical 110 and thoracic portions 120. Intermediate portion 130 could comprise any commercially practical length, and preferably has a minimum end-to-end length of at least 10 cm. All commercially suitable material(s) are contemplated to comprise intermediate portion 130 including, for example, plastics and other polycarbonates, metals, woods, synthetics, and/or any combinations thereof. Preferred intermediate portions are sufficiently rigid to maintain a fixed angular relationship within a 10° tolerance between a superior 111 and inferior end 112 of intermediate portion 130. Optionally, intermediate portion could comprise a telescoping region (not shown).

First adjustment region 140 is disposed between the cervical 110 and intermediate portions 130, and provides relative movement of the cervical 110 and intermediate portions 130. Second 150 adjustment region is disposed between the intermediate 130 and thoracic portions 120, and provides relative movement of the intermediate 130 and thoracic portions 120. Each of the adjustment regions 140 and 150 preferably provides at least 15° of relative movement between their respective portions. Optionally, at least one of the adjustment regions can provide at least 25°, and more preferably, at least 30° of relative movement between the respective portions. Thus, the first 140 and second 150 adjustment regions could each be constructed to provide an equivalent or different degree of rotation between their respective portions. For example, the first adjustment region might provide 25° of relative movement, while the second adjustment region might provide 32° of relative movement.

Preferably, as shown in FIGS. 1-2, adjustment regions 140 and 150 each compose a pivot 180 and 190, respectively, although any commercially available structures that replicate the function of a pivot (e.g., flexible or bendable portions) are also contemplated, as discussed above. Adjustment regions 140 and 150 advantageously allow for the adjustment of the cervical and thoracic portions to comfortably accommodate differently proportioned wearers, while coupling the portions and assisting in preventing movement of the head and neck.

CTO 100 further comprises connector portion 170, which is disposed between the cervical 110 and intermediate portions 130. An end of connector portion 170 and an end of intermediate portion 130 preferably compose pivot 180, which defines first adjustment region 140. At least one clip (e.g., snap) 175 attaches first adjustment region 140 to cervical portion 110. However, other fastener(s) are also contemplated including, for example, mechanical fasteners (e.g., hook and loop fasteners, buckles, buttons, clasps, etc.), non-mechanical fasteners (e.g., adhesives, magnets, etc.), and/or any combinations thereof Alternatively, first adjustment region could be attached to the cervical portion by one or more fasteners (not shown) without use of an adapter portion.

Figure 3A:
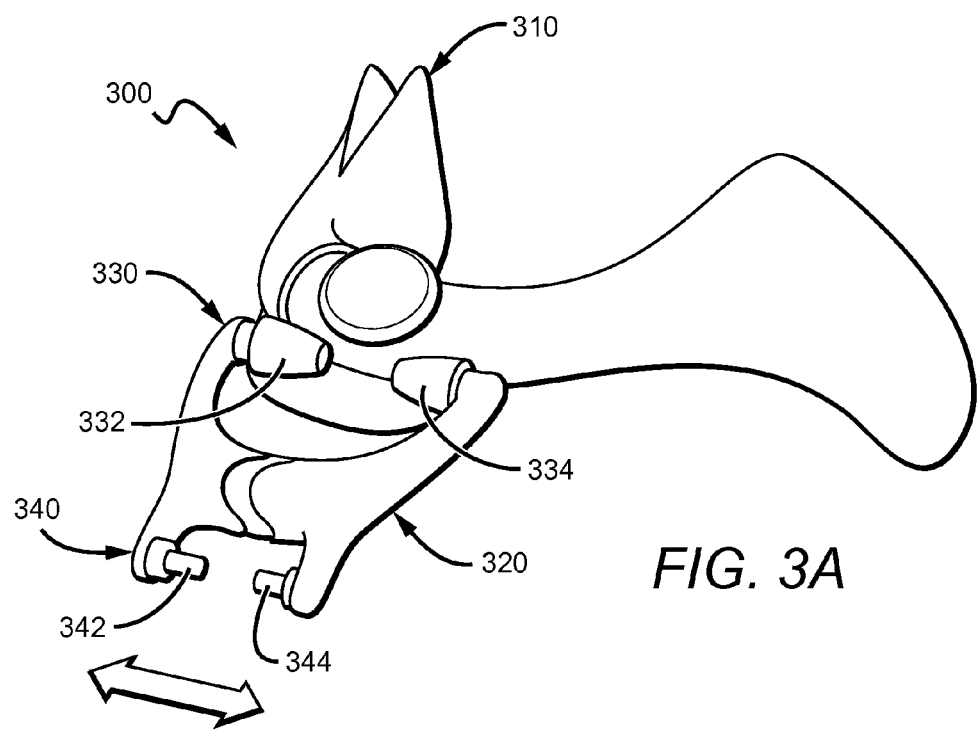
FIGS. 3A and 3B are illustrations of the "opened" and "closed" positions of the adjustment regions, respectively.
Figure 3B:
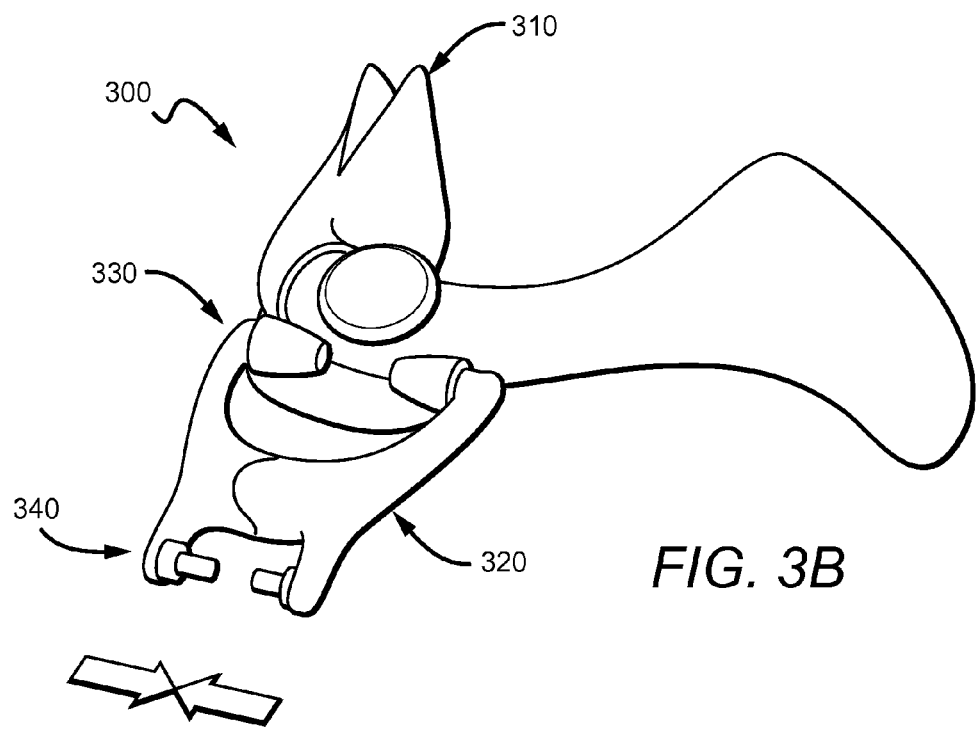

In another contemplated embodiment shown in FIGS. 3A and 3B, a CTO 300 is shown comprising a cervical portion 310, an intermediate portion 320, and first and second adjustment regions 330 and 340. The first adjustment region 330 couples the cervical 310 and intermediate portions 320, and comprises a first 332 and second locking device 334. Similarly, the second adjustment region 340 couples the intermediate portion to a thoracic portion (not shown), and comprises a third 342 and fourth locking device 344. The adjustment regions can move laterally from a "opened" to a "closed" position (compare FIG. 3A with FIG. 3B). Thus for example, in the "opened" or outward position shown in FIG. 3A, the first adjustment region 330 allows for relative movement of the cervical 310 and intermediate portions 320. In contrast, in the "closed" or inward position shown in FIG. 3B, the first adjustment region 330 prevents relative movement of the portions 310 and 320.

FIG. 3A shows the locking devices 332, 334, 342, and 344 of the first and second adjustment regions 330 and 340 in an "opened" position. To lock the relative positions of the cervical, intermediate, and thoracic portions, the adjustment regions are moved laterally to a "closed" position, as shown in FIG. 3B. Each of the locking devices can comprise a latch or other fastener to retain the locking device in either the "opened" or "closed" position. In one aspect, a spring or other commercially suitable elastic device (not shown) can advantageously be disposed within each of the locking devices, such that the locking device has a bias in either an unlocked (e.g., "opened") or locked (e.g., "closed") position.

FIGS. 3C and 3D depict a side and frontal view of locking device 332, which comprises a first 332A and second splined portion 332B. Each of the splined portions 332A and 332B comprise a plurality of splines 350 (e.g., teeth or other projections). Preferably, the splined portions 332A and 332B are configured to be complementary such as to receive one another in interlocking engagement. Thus, for example, first splined portion 332A comprises external splines, while second spline portion 332B comprises internal splines. However, all commercially suitable configurations are contemplated.

In FIG. 4, a method of coupling a cervical orthotic with a thoracic orthotic on a wearer is disclosed. Initially, the cervical and thoracic orthotics are coupled with first and second pivots to compose a CTO. Optionally, coupling the first cervical and thoracic orthotics could include snap coupling the cervical orthotic with an intermediate piece that includes the first pivot. Preferably, the cervical and thoracic orthotics are coupled by disposing first and second intermediate pieces between the cervical and thoracic orthotics. However, any commercially suitable method of coupling the cervical and thoracic orthotics is contemplated.

Next, the CTO of FIG. 4 is designed to allow each pivot to be continuously operable while the CTO is being adjusted, and then locked in a desirable angular position. Optionally, a telescoping region could be provided between the cervical and thoracic orthotics.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An orthosis comprising:
   a cervical portion;
   a thoracic portion;
   an intermediate portion disposed intermediate the cervical and thoracic portions;
   a first splined adjustment region configured to provide at least 15° of relative movement between the cervical and intermediate portions; and
   a second splined adjustment region configured to provide at least 15° of relative movement between the intermediate and thoracic portions.

2. The orthosis of claim 1, wherein at least one of the first and second splined adjustment regions is biased into an open position.

3. The orthosis of claim 1, wherein the splines are internal.

4. The orthosis of claim 1, wherein the splines are lateral.

5. The orthosis of claim 1, wherein the splined adjustment region has a coarseness of between 10-30 positions.

6. The orthosis of claim 1, wherein at least one of the first and second adjustment regions comprises a pivot.

7. The orthosis of claim 6, further comprising an adaptor portion disposed between the cervical portion and the intermediate portion, and the pivot is composed of ends of the adaptor portion and the intermediate portion.

8. The orthosis of claim 6, wherein the first adjustment region removably attaches to the cervical portion using a clip.

9. The orthosis of claim 1, wherein the first adjustment region achieves the relative movement between the cervical and intermediate portions by bending.

10. The orthosis of claim 1, wherein at least one of the first and second adjustment regions provides at least 25° of the relative movement between the cervical and intermediate portions and the thoracic and intermediate portions, respectively.

11. The orthosis of claim 6, wherein the second adjustment region removably attaches to the thoracic portion using a clip.

12. The orthosis of claim 1, wherein the second adjustment region achieves the relative movement between the cervical and intermediate portions by bending.

13. The orthosis of claim 1, wherein the intermediate portion has a superior end and an inferior end, and is sufficiently rigid to maintain a fixed angular relationship between the ends within a 10° tolerance.

14. The orthosis of claim 1, wherein the intermediate portion has a minimum end-to-end length of at least 10 cm.

15. The orthosis of claim 1, wherein the thoracic portion has a telescoping region.

16. The orthosis of claim 1, wherein the first adjustment region provides at least 30° of the relative movement between the cervical and intermediate portions, and the second adjustment region provides at least 30° of the relative movement between the thoracic and intermediate portions.

17. A method of coupling a cervical orthotic with a thoracic orthotic on a wearer, comprising
   coupling the cervical and thoracic orthotics with first and second pivots to compose a cervico-thoracic orthotic, where each of the first and second pivots comprises a splined adjustment region; and
   operating the cervico-thoracic orthotic such that each of the pivots is continuously operable while the cervico-thoracic orthotic is being worn by the wearer.

18. The method of claim 17, further comprising snap coupling the cervical orthotic with an intermediate piece that includes the first pivot.

19. The method of claim 17, further comprising providing a telescoping region between the cervical and thoracic orthotics.

20. The method of claim 17, wherein the step of coupling comprises disposing first and second intermediate pieces between the cervical and thoracic orthotics.

* * * * *